(12) United States Patent
Bjaerum et al.

(10) Patent No.: US 7,245,746 B2
(45) Date of Patent: Jul. 17, 2007

(54) ULTRASOUND COLOR CHARACTERISTIC MAPPING

(75) Inventors: Steinar Bjaerum, Horten (NO); Bjorn Olstad, Stathelle (NO); Kjell Kristofferson, Oslo (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 647 days.

(21) Appl. No.: 10/064,032

(22) Filed: Jun. 4, 2002

(65) Prior Publication Data

US 2002/0186868 A1   Dec. 12, 2002

Related U.S. Application Data

(60) Provisional application No. 60/297,572, filed on Jun. 12, 2001.

(51) Int. Cl.
*G06K 9/00* (2006.01)
(52) U.S. Cl. ............ 382/128; 382/107; 382/168; 382/171; 382/274; 600/437
(58) Field of Classification Search ........ 382/103, 382/107, 128, 168, 171, 172, 274; 128/922; 600/437–449
See application file for complete search history.

(56) References Cited

U.S. PATENT DOCUMENTS

| | | | |
|---|---|---|---|
| 5,622,174 A * | 4/1997 | Yamazaki | 600/441 |
| 5,628,321 A | 5/1997 | Scheib et al. | |
| 5,718,229 A * | 2/1998 | Pesque et al. | 600/441 |
| 5,820,561 A | 10/1998 | Olstad et al. | |
| 5,846,202 A | 12/1998 | Ramamurthy et al. | |
| 5,910,119 A | 6/1999 | Lin | |
| 6,017,309 A * | 1/2000 | Washburn et al. | 600/454 |
| 6,071,241 A | 6/2000 | Washburn et al. | |
| 6,120,451 A | 9/2000 | Washburn et al. | |
| 6,126,605 A | 10/2000 | Washburn et al. | |
| 6,162,176 A | 12/2000 | Washburn et al. | |
| 6,176,828 B1 * | 1/2001 | Becker et al. | 600/440 |
| 6,368,277 B1 | 4/2002 | Mao et al. | 600/441 |
| 6,447,453 B1 | 9/2002 | Roundhill et al. | 600/443 |
| 6,558,324 B1 * | 5/2003 | Von Behren et al. | 600/440 |

\* cited by examiner

*Primary Examiner*—Bhavesh M Mehta
*Assistant Examiner*—Christopher Lavin
(74) *Attorney, Agent, or Firm*—McAndrews, Held & Malloy, Ltd.; Peter J. Vogel; Michael A. Dellapenna (57) ABSTRACT

An ultrasound machine is disclosed that displays a color representation of moving structure, such as a cardiac wall tissue, within a region of interest on a monitor. The color representation is generated by displaying at least one color characteristic corresponding to a movement parameter of the structure, such as velocity or strain rate. The movement parameter is mapped to the color characteristic by apparatus comprising a front-end that generates received signals in response to ultrasound waves. A Doppler processor generates a set of parameter signals representing values of the movement parameter within the structure. A control processor adaptively generates a mapping function based on the distribution of the parameter signals to map the parameter signals to a set of color characteristic signals. A display processor applies the mapped values of the color characteristic legend to the values of the movement parameter representing the moving structure, to display a color representation on the monitor in response to the mapping function.

22 Claims, 4 Drawing Sheets

MYOCARDIUM TISSUE STRUCTURE 105

ROI 86

SEPTUM

APICAL 4-CHAMBER VIEW OF HEART

ORIGINAL     ADAPTIVE

ULTRASOUND COLOR CHARACTERISTIC MAPPING

CROSS REFERENCE TO RELATED APPLICATIONS

The applicants claimed priority based on provisional application No. 60/297,572 filed Jun. 12, 2001 in the names of Bjorn Olstad, Steinar Bjaerum, and Kjell Kristoffersen.

BACKGROUND OF INVENTION

Certain embodiments of the present invention relate to an ultrasound machine for generating and displaying an image of moving structure. More particularly, certain embodiments relate to adaptively color mapping an image of moving structure such as heart tissue.

Echocardiography is a branch of the ultrasound field that is currently a mixture of subjective image assessment and extraction of key quantitative parameters. Evaluation of cardiac wall function has been hampered by a lack of well-established parameters that may be used to increase the accuracy and objectivity in the assessment of, for example, coronary artery diseases. Stress echo is such an example. It has been shown that the subjective part of wall motion scoring in stress echo is highly dependent on operator training and experience. It has also been shown that inter-observer variability between echo-centers is unacceptably high due to the subjective nature of the wall motion assessment.

Much technical and clinical research has focused on the problem and has aimed at defining and validating quantitative parameters. Encouraging clinical validation studies have been reported, that indicate a set of new potential parameters that may be used to increase objectivity and accuracy in the diagnosis of, for instance, coronary artery diseases. Many of the new parameters have been difficult or impossible to assess directly by visual inspection of the ultrasound images generated in real-time. The quantification has typically required a post-processing step with tedious, manual analysis to extract the necessary parameters.

Much of the prior art describes techniques for non-adaptive color mapping of estimated imaging parameters such as tissue velocity and strain rate. A fixed mapping of a continuous range of color hues is typically used to indicate positive velocities or strain rates and a second fixed mapping of a continuous range of color hues is used to indicate negative velocities or strain rates. This type of color encoding makes it easy to identify reversals in velocities or strain rates. Timing information related to the velocity or strain rate reversals is also easy to extract from M-mode displays.

However, the non-adaptive color schemes in the prior art are not well suited for visual determination of other parameters, such as quantitative velocities or strain rates. Typically, a Nyquist velocity and associated pulse repetition frequency is set in order to avoid aliasing. Most of the actual velocities present are only a small fraction of the peak velocity which, in cardiac imaging from apex, typically may be measured at the mitral ring during the E-wave in diastole. As a result, most regions in the image are mapped with only small variations of the color hue mapped to lower positive and/or lower negative velocities. Quantitative assessment of parameters such as velocities or strain rates from 2-D images has been difficult, even in lucky situations, with a good spread of measured imaging parameters. It has, therefore, been necessary to resort to post-processing techniques and manual extraction of the digital information used in the color encoding for estimation of quantitative values.

Certain adaptive techniques have been previously applied to flow signals. For example, a method in U.S. Pat. No. 6,017,309 to Washburn et al. describes color coding of color flow data relating to fluid, such as blood. As explained in Col. 8, lines 25-54, an Auto Color Map Threshold/Compression Algorithm allows the stored color map threshold to be reset for better detection of low velocity or low power flow and allows the map to be re-mapped or compressed over the range of color flow data actually present. Two algorithms are provided: one for velocity mode and one for PDI mode. For the velocity mode, N frames of color flow data are collected from cine memory 28C and formed into a composite histogram as shown in FIG. 8. The N frames are required to account for flow pulsatility. Then, the fixed map threshold is received by the algorithm from memory at a terminal 31 and is adjusted, if necessary, and the color map is re-created to apply more colors of the map across the full range of data in the composite histogram in a linear manner. As FIG. 8 shows, the positive velocity data in the composite histogram does not cover the full range of 0 to 127, but instead covers some smaller range in-between. The algorithm calculates the statistics of the histogram data and sets the new map threshold to be x standard deviations below the mean. The value of x is determined per application to maximize low velocity flow detection while minimizing low velocity artifacts such as residual wall or tissue motion. The negative map threshold similarly is set for negative velocities based on the statistics of the negative velocity histogram. In this example of FIG. 8, the velocity color map is re-created (effectively linearly compressed) to apply more of its colors across the range of data in the composite histogram, taking into account the map threshold as a reference end point.

Methods in U.S. Pat. No. 6,071,241 to Washburn et al., U.S. Pat. No. 6,126,605 to Washburn et al., and U.S. Pat. No. 6,162,176 to Washburn et al., each describe an ultrasound color flow imaging system programmed to optimize display images of power and velocity by automatically adjusting thresholds by using histograms and samplings of color flow data.

A method in U.S. Pat. No. 6,120,451 to Washburn et al. describes an ultrasound color flow imaging system programmed to optimize display images of power and velocity by automatically adjusting thresholds by using histograms.

None of the foregoing patents, however, describe or suggest any color mapping technique for generating an ultrasound display of moving structure that uses the full dynamic range of the color map. The foregoing patents relate to displays representing moving fluid, such as blood and only perform simple linear compressions of the color map dynamic range or pre-determined non-linear compressions.

A need exists for a robust approach to more easily visualize tissue motion parameter information, such as strain rate, in a two-dimensional ultrasound image such that more of the tissue motion parameter information is broken out and is observed.

SUMMARY OF INVENTION

An embodiment of the present invention provides an ultrasound system for generating an image responsive to moving cardiac structure by adaptively generating a mapping function based on parameter signals and mapping the parameter signals to a set of color characteristic signals.

An apparatus is provided in an ultrasound machine for generating a display responsive to moving structure within a region of interest (ROI) of a subject by displaying at least one color characteristic corresponding to a movement parameter of the structure. In such an environment the apparatus for mapping the color characteristic preferably comprises a front-end arranged to generate transmitted signals into the structure and then to generate received signals in response to ultrasound waves backscattered from the structure in the ROI over a time period. A processor is responsive to the received signals to generate a set of parameter signals representing values of the movement parameter within the structure during at least a portion of the time period and is responsive to a distribution of the set of parameter signals and a mapping algorithm to generate a set of color characteristic signals representative of the values of the movement parameter. A display is arranged to display a color representation of the moving structure in response to the color characteristic signals. The resultant mapping is dependent, in part, on the distribution of values of the movement parameter and, therefore, the embodiment is adaptive.

A method is also provided in an ultrasound machine for generating a display responsive to moving structure within a region of interest of a subject by displaying at least one color characteristic corresponding to a movement parameter of the structure. In such an environment, the method preferably comprises transmitting signals into the structure and receiving signals in response to ultrasound waves backscattered from the structure in the region of interest over a time period. A set of parameter signals representing values of the movement parameter within the structure during the time period is generated in response to the received signals. A mapping function generates a set of color characteristic signals representative of the values of the movement parameter in response to a distribution of the set of parameter signals and a mapping algorithm. A color representation of the moving structure is displayed in response to the set of color characteristic signals. The resultant mapping is dependent, in part, on the distribution of values of the movement parameter and, therefore, the embodiment is adaptive.

Certain embodiments of the present invention afford an approach to more easily visualize tissue motion parameter information, such as tissue velocity and strain rate, in a two-dimensional ultrasound image such that more of the tissue motion parameter information is broken out and observed.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION

An embodiment of the present invention enables adaptive color mapping of moving tissue structure based on the distribution of movement parameter data. As used in this specification and claims, structure means non-liquid and non-gas matter, such as cardiac wall tissue. An embodiment of the present invention offers improved, real-time visualization and assessment of wall tissue function. The moving structure is characterized by a movement parameter, which means a parameter derived from movement of the structure, such as velocity or strain rate.

Figure 1:
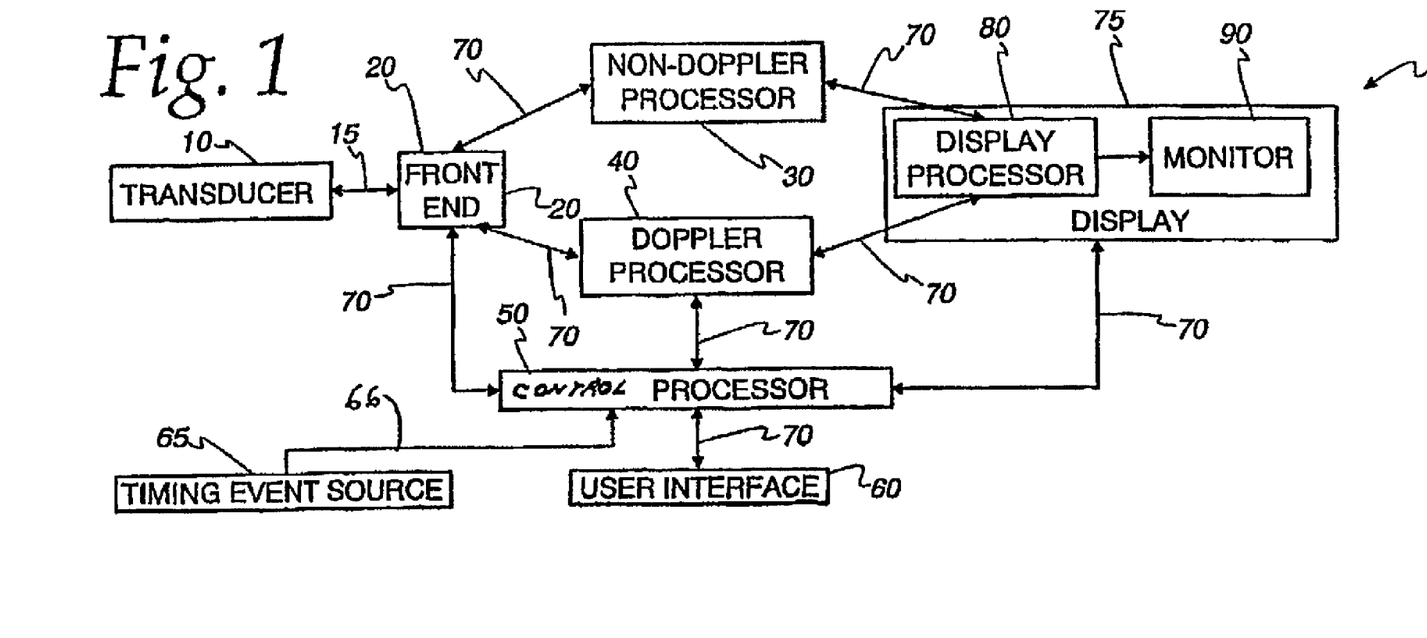
FIG. 1 is a schematic block diagram of an ultrasound machine made in accordance with an embodiment of the present invention.

FIG. 1 is a schematic block diagram of an embodiment of the present invention comprising an ultrasound machine 5. A transducer 10 is used to transmit ultrasound waves into a subject by converting electrical analog signals to ultrasonic energy and to receive ultrasound waves backscattered from the subject by converting ultrasonic energy to analog electrical signals. A front-end 20 comprising a receiver, transmitter, and beamformer, is used to create the necessary transmitted waveforms, beam patterns, receiver filtering techniques, and demodulation schemes that are used for the various imaging modes. Front-end 20 performs the functions by converting digital data to analog data and vice versa. Front-end 20 interfaces at an analog interface 15 to transducer 10 and interfaces over a digital bus 70 to a non-Doppler processor 30, a Doppler processor 40, and a control processor 50. Digital bus 70 may comprise several digital sub-buses, each sub-bus having its own unique configuration and providing digital data interfaces to various parts of the ultrasound machine 5.

Non-Doppler processor 30 comprises amplitude detection functions and data compression functions used for imaging modes such as B-mode, B M-mode, and harmonic imaging. Doppler processor 40 comprises clutter filtering functions and movement parameter estimation functions used for imaging modes such as tissue velocity imaging (TVI), strain rate imaging (SRI), and color M-mode. The two processors, 30 and 40, accept digital signal data from the front-end 20, process the digital signal data into estimated parameter values, and pass the estimated parameter values to processor 50 and a display 75 over digital bus 70. The estimated parameter values may be created using the received signals in frequency bands centered at the fundamental, harmonics, or sub-harmonics of the transmitted signals in a manner known to those skilled in the art.

Display 75 comprises scan-conversion functions, color mapping functions, and tissue/flow arbitration functions, performed by a display processor 80 which accepts digital parameter values from processors 30, 40, and 50, processes, maps, and formats the digital data for display, converts the digital display data to analog display signals, and passes the analog display signals to a monitor 90. Monitor 90 accepts the analog display signals from display processor 80 and the resultant image is displayed to the operator on monitor 90.

A user interface 60 allows user commands to be input by the operator to the ultrasound machine 5 through control processor 50. User interface 60 comprises a keyboard, mouse, switches, knobs, buttons, track ball, and on screen menus (not shown).

A timing event source 65 may be used to generate a cardiac timing event signal 66 that represents the cardiac waveform of the subject. The timing event signal 66 is input to ultrasound machine 5 through control processor 50.

Control processor 50 is the main, central processor of the ultrasound machine 5 and interfaces to various other parts of the ultrasound machine 5 through digital bus 70. Control processor 50 executes the various data algorithms and functions for the various imaging and diagnostic modes. Digital data and commands may be transmitted and received between control processor 50 and other various parts of the ultrasound machine 5. As an alternative, the functions performed by control processor 50 may be performed by multiple processors, or may be integrated into processors 30, 40, or 80, or any combination thereof. As a further alternative, the functions of processors 30, 40, 50, and 80 may be integrated into a single PC backend.

Figure 2:
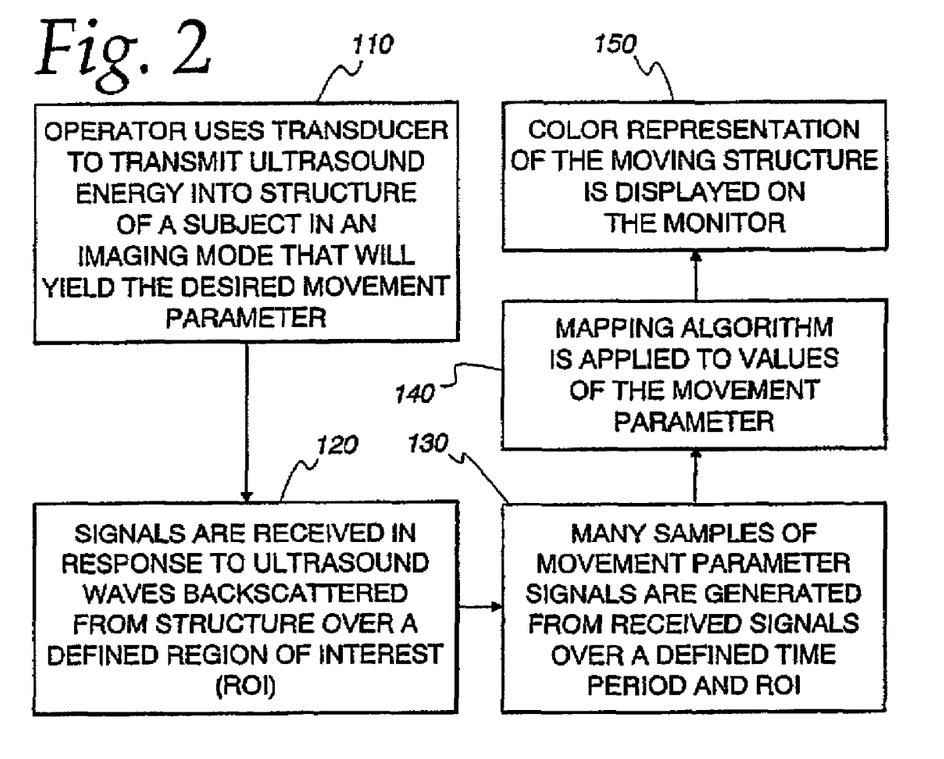
FIG. 2 is a flowchart of a method performed by the machine shown in FIG. 1 in accordance with an embodiment of the present invention.

Referring to FIG. 2, in step 110 an operator uses transducer 10 to transmit ultrasound energy into anatomical structure, such as cardiac tissue 105 (see FIG. 4a), of the subject in an imaging mode, such as tissue velocity imaging (TVI), that will yield the desired estimated movement parameter values of the desired anatomical structure (typically a 2-dimensional apical cross section of the heart). Ultrasound energy is received into transducer 10 and signals are received into front-end 20 in response to ultrasound waves backscattered from the structure. The resultant estimated movement parameter values computed by Doppler processor 40 typically comprise longitudinal estimates of mean tissue velocity or strain rate.

Figure 3:
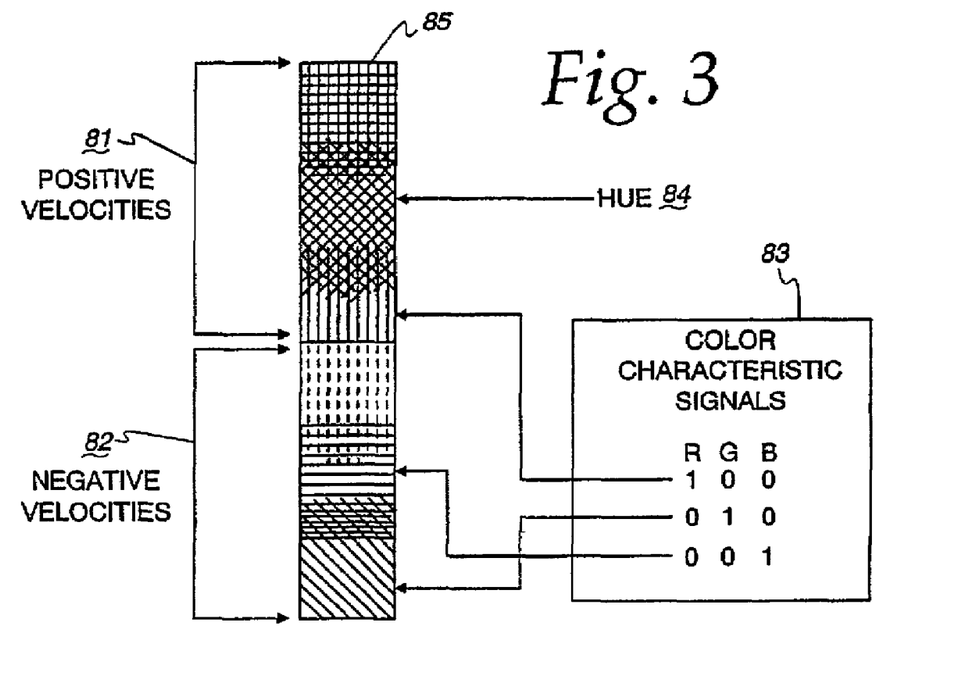
FIG. 3 illustrates an exemplary color characteristic legend, comprising continuously varying hues of color, and is presented on the display shown in FIG. 1 in accordance with an embodiment of the present invention.

In order to help the operator interpret the movement parameter, a color characteristic legend is displayed on monitor 90. Referring to FIG. 3, in TVI mode, the color legend employs a fixed, continuous range of color hues to indicate positive velocities and a second fixed, continuous range of color hues is used to indicate negative velocities. Typically, red/yellow hues show anatomical motion towards the transducer 10 and blue/green hues show motion away from the transducer 10. These color hues 84 are illustrated in the color characteristic legend 85 shown in FIG. 3. The various cross-hatchings and lines in the color characteristic legend 85 of FIG. 3 represent a continuous range of color hues. Going from the top of the color characteristic legend 85 to the bottom, the colors transition from yellow to orange to red representing the positive velocity segment 81 of the color characteristic legend 85 and then violet to blue to green, representing the negative velocity segment of the color characteristic legend 85. However, the color hues 84 that make up the color characteristic legend 85 may be any continuous or semi-continuous range of colors that provide good discrimination between levels of the movement parameter. The portions of FIG. 3 in which cross-hatched lines intersect represent a blending of color hues.

Figures 4A, 4B, 4C, 5:
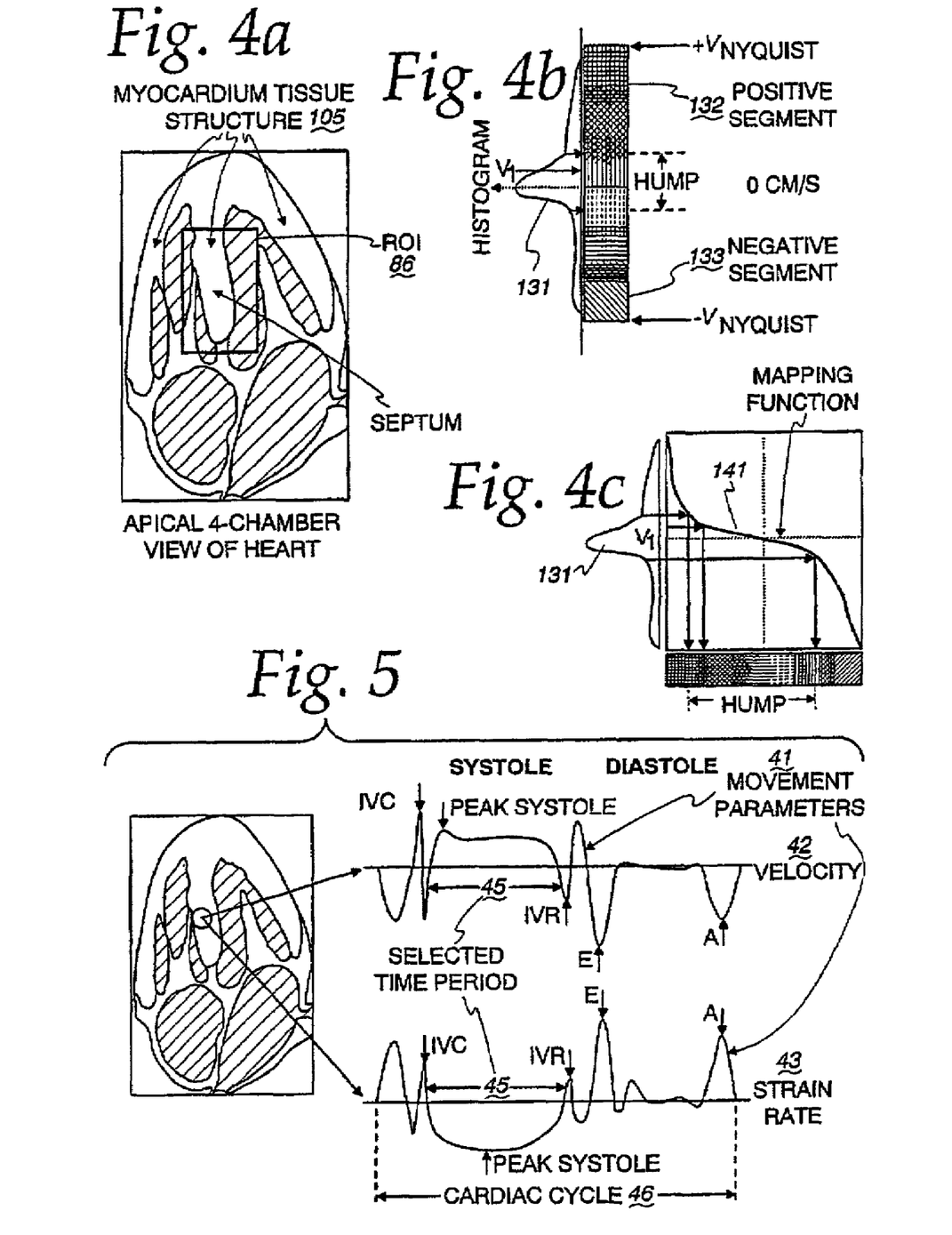
FIG. 4a is a schematic cross-sectional view of the human heart including myocardium tissue bounded by a region of interest (ROI) that is designated by the machine shown in FIG. 1 in accordance with an embodiment of the present invention.
FIG. 4b is an exemplary histogram representing the frequency of occurrence of estimated velocity values of samples of tissue within the ROI of FIG. 4a, generated by the machine shown in FIG. 1 in accordance with an embodiment of the present invention.
FIG. 4c shows a resultant form of a mapping function that maps the histogram of FIG. 4b to an exemplary color characteristic legend according to a mapping algorithm executed by the machine shown in FIG. 1 in accordance with an embodiment of the present invention.
FIG. 5 is a schematic cross-sectional view of the heart shown in FIG. 4a also illustrating typical velocity and strain rate profiles as a function of time, measured longitudinally in an apical view in accordance with an embodiment of the present invention.

The histogram 131 of FIG. 4b illustrates how typical velocity measurements in the myocardium of the heart 105 will be distributed. Low positive and low negative velocities, compared to the peak velocities, dominate the frequency distribution as is seen by the hump in the histogram 131. The peak velocities only occur for a short period of time. As illustrated in FIG. 5, typical velocity and strain rate values at specific points are plotted as a function of time. Apical images contain a large spatial gradient in the velocities. Peak velocities are both spatially and temporally localized and represent only a minor part of the histogram 131.

In Step 120 of FIG. 2, ultrasound energy is received into transducer 10 and signals are received into front-end 20 in response to ultrasound waves backscattered from the structure 105 of a subject over an operator-defined region of interest (ROI) 86 (see FIG. 4a). The operator brings up a scaleable ROI 86 on monitor 90 through the user interface 60 to select a spatial or anatomical region to process such as the septum of the heart (see FIG. 4a). The ROI may be chosen to cover the entire displayed image if desired. Such a positioning of an ROI 86 forces the subsequent processing to segment and optimize the displayed image for that specific region.

In other similar embodiments, the ROI 86 may be selected automatically or as a combination of manual and automatic methods. For example, an algorithm for automatic positioning of an ROI 86 may be designed and embedded in the control processor 50 to separate the myocardium from cavities by using well-known segmentation and thresholding techniques operating on the data of the movement parameter.

In Step 130 of FIG. 2, received signals are sent from front-end 20 to Doppler processor 40 over digital bus 70. Doppler processor 40 generates many samples of movement parameter signals, such as velocity or strain rate, using the well-known imaging modes of TVI and SRI over a segmented time period 45 (see FIG. 5) based on the received signals corresponding to the region designated by ROI 86. The operator selects, through the user interface 60, a desired time interval 45 to process, such as systole, which is a sub-interval of the cardiac cycle 46 (see FIG. 5). These time intervals are determined from well-known timing event sources 65 (FIG. 1) and techniques such as electrocardiogram (ECG) techniques and/or from characteristic signatures in the profiles of the movement parameter data. Those skilled in ultrasound also know how to derive timing events from signals of other sources such as a phonocardiogram signal, a pressure wave signal, a pulse wave signal, or a respiratory signal. Ultrasound modalities such as spectral Doppler or M-modes may also be used to obtain cardiac timing information.

It may be advantageous to select a time interval 45 corresponding to a complete cardiac cycle 46 in order to optimize the display for the entire cardiac cycle 46. Another possibility is to limit the time interval 45 to the systolic time period in order to display a color representation that is optimized for optimal systolic visualization. Other sub-intervals of the cardiac cycle 46 may also be applied. FIG. 5 illustrates typical velocity 42 and strain rate 43 profiles which may be segmented into desired time periods based on profile features. For reference, the profiles in FIG. 5 are annotated with the times corresponding to: IVC=isovolumetric contraction, IVR=isovolumetric relaxation, E=early diastolic velocity, and A=late diastolic velocity.

The time interval 45 may be selected automatically or as a combination of manual and automatic methods. For example, the time period may be determined automatically with an algorithm embedded in control processor 50. The algorithm may use well-known techniques of analyzing estimated parameter profiles looking for key signature characteristics and defining a time period based on the characteristics or, similarly, analyzing the ECG signal. An automatic function may be implemented to recognize and exclude unwanted events from the selected time period, if desired, as well.

Figure 6:
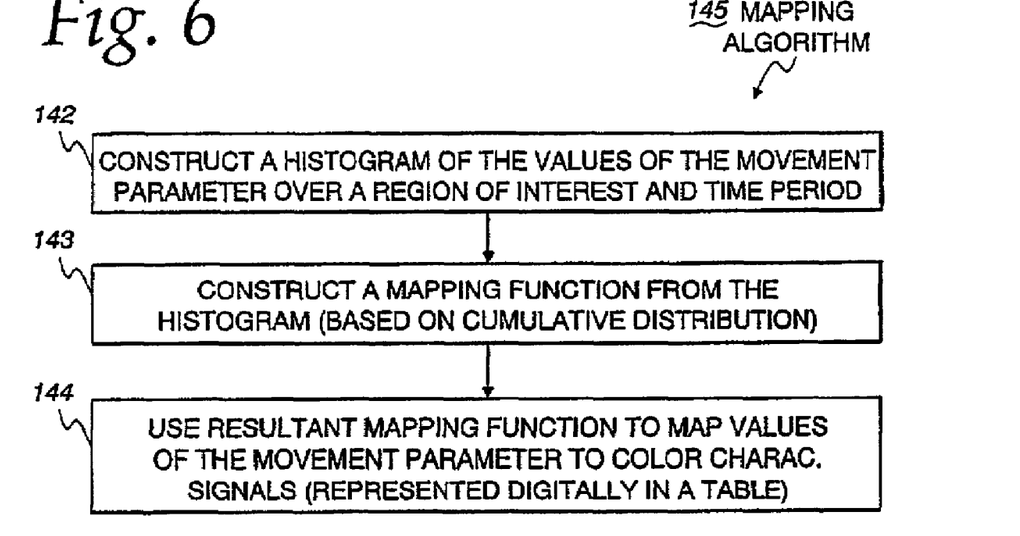
FIG. 6 is a flowchart of a mapping algorithm for adaptive mapping of a set of color characteristic signals, resulting in the mapping function shown in FIG. 4c in accordance with an embodiment of the present invention.

In Step 140 of FIG. 2, the values of the movement parameter are sent from Doppler processor 40 to control processor 50, where a mapping algorithm 145 (see FIG. 6) is applied to the values of the movement parameter. FIG. 6 is a flow chart of the mapping algorithm 145.

In Step 142 of the mapping algorithm 145, a histogram 131 is constructed from the many samples of the values of the movement parameter (see FIG. 4b), restricted to those samples from the ROI 86 and the time interval 45. This histogram 131 represents the frequency of occurrence of the values of the movement parameter. The histogram 131 may be constructed with or without weightings based on measurements of the values of the movement parameter (e.g. velocity or strain rate values). In one embodiment of the present invention, the positive 132 and negative 133 values of the movement parameter are processed separately, but in a similar manner, to construct the histogram 131. An alternative is to construct a single histogram 131 for absolute values of the movement parameter instead of processing positive 132 and negative 133 values of the movement parameter separately. Such a single histogram 131 will make the final displayed color representation maintain visual separation of absolute differences between magnitudes of positive and negative movement relative to each other.

In Step 143 of the mapping algorithm 145, a mapping function 141 is constructed by control processor 50 (see FIG. 4c). This mapping function 141 is formed by generating a cumulative total of the frequency of occurrence of the values of the movement parameter 41 in the histogram 131, and then normalizing the cumulative total to the domain of the color characteristic legend 85. The result is a uniform distribution of the values of the movement parameter across the domain of the color characteristic legend 85. As an option, the cumulative total may be weighted based on characteristics of the histogram 131. Alternative transfer functions may be implemented as well, resulting in other distributions of the values of the movement parameter across the domain of the color characteristic legend 85.

In Step 144 of the mapping algorithm 145, the resultant mapping function 141 is used by control processor 50 as a non-linear transfer function between the values of the movement parameter (e.g. 42 or 43) and the values of the color hues 84 in the color characteristic legend 85 (see FIG. 4c). The process is illustrated by the arrows shown in FIG. 4c, for a particular estimated velocity value. It may be seen, in FIG. 4c, that the location within the color characteristic legend that the particular velocity value $V_1$ now gets mapped to is different from the location within the color characteristic legend $V_1$ was mapped to originally in FIG. 4b, before creation of the new mapping function 141. The frequency of occurrence of the values of the movement parameter now have a proportional relationship to the number of color hues 84 in the color characteristic legend 85.

For example, the center portion (hump) of the histogram 131, which contains most of the samples of velocity estimates, is now mapped over a broader range of color hues. Also, each fixed proportion of the hues 84 of the color characteristic legend 85 will occupy roughly the same amount of spatial locations in the image (i.e results in a uniform distribution of the values of the movement parameter across the domain of the color characteristic legend). The relationship between the values of the movement parameter and the color hues 84 is typically represented in a digital table in the memory of control processor 50 and transferred to the memory in display processor 80 over digital bus 70.

The color hues are typically represented in memory as red, green, blue (RGB) values as shown in FIG. 3. The RGB values constitute the color characteristic signals 83. The RGB values may be represented as normalized values between 0 and 1, as shown in FIG. 3. Therefore, to represent a perfectly red hue, the RGB values are (1 0 0). For a perfectly green hue, the RGB values are (0 1 0), and for blue (0 0 1). Any other color hue may be represented by various combinations of RGB values. For example, if an RGB value is (0.5 0.8 0.3), the combination of unequal parts of red, green, and blue hues each with a different weighting results in some new color hue.

An RGB combination of (1 1 1) yields a perfectly white hue and an RGB combination of (0 0 0) yields a perfectly black hue.

Live imaging may be temporarily suspended for a short period of time (e.g. a couple seconds) while the values of the movement parameter are segmented and processed, depending on the exact architecture and capabilities of the ultrasound machine 5.

Figure 7:
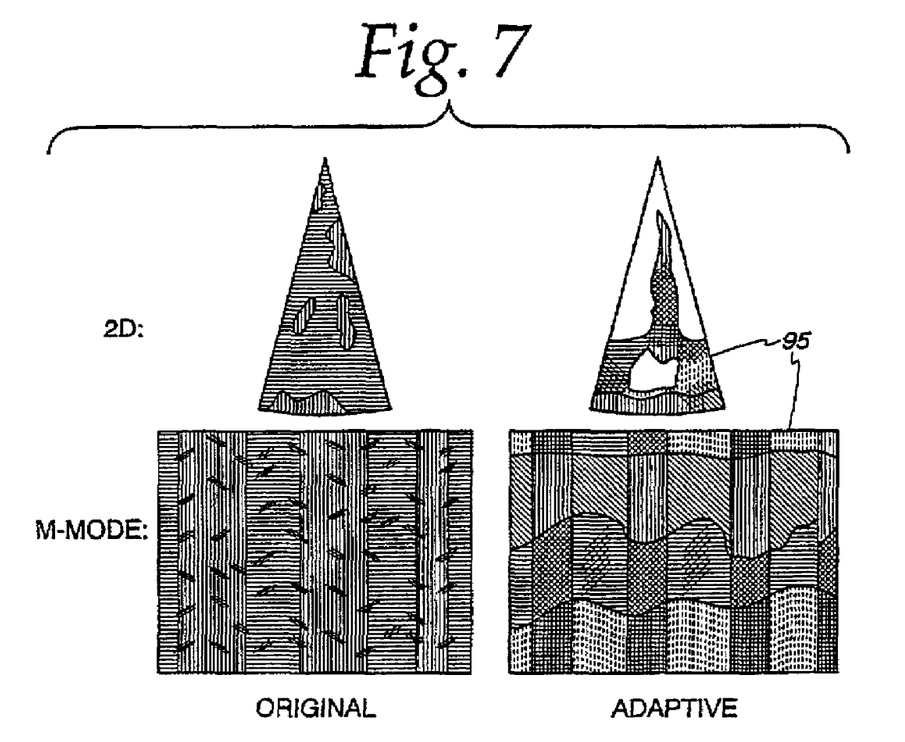
FIG. 7 shows sector and M-mode displays generated by the machine shown in FIG. 1 and illustrates the effect of applying the resultant adaptive color characteristic mapping algorithm for a tissue velocity example in accordance with an embodiment of the present invention.

In Step 150 of FIG. 2, live imaging resumes with the new color characteristic mapping (color-mapping table) being applied to new values of the movement parameter (e.g. 42 or 43) in display processor 80. A color representation 95 of the moving structure 105 is displayed on monitor 90 as seen in FIG. 7. The new mapping causes the color characteristic legend 85 to represent actual values of the movement parameters in a non-linear manner. However, movement parameter values are broken out from each other much better, allowing for better observation of the movement parameter values present in the ROI.

FIG. 7 illustrates the effect of the adaptive color characteristic mapping function 141 for a tissue velocity imaging example. The original image on the left is dominated by red and blue color hues (represented by the vertical and horizontal lines) indicating lower velocities relative to the Nyquist velocity. The right hand side of the figure illustrates the same data set with an adaptively determined color-mapping table applied. It may be seen in FIG. 7 that the images on the right contain many more color hues (represented by the various vertical, horizontal, and diagonal lines and the various cross-hatchings and dashed lines) compared to the images on the left, thus allowing for better visual quantification of the movement parameter by the operator.

Strain rate adaptive color mapping may follow exactly the same method as tissue velocity adaptive color mapping. In addition, it may be possible to reserve a unique color hue for small spatial deformations under a preset strain rate threshold. The described mapping algorithm 145 would then be limited to operate on the strain rate values exceeding the threshold value.

As an option, the mapping algorithm may be designed such that movement parameter values of zero, such as zero velocity and zero strain rate, are always mapped to a fixed color hue. Also, as a further option, the mapping algorithm may be designed such that the movement parameter of a tracked anatomical location is mapped to a fixed color hue. As a result, mapping an endocardial or epicardial location, for example, would generate a standardized color representation of cardiac wall thickening.

An embodiment of the method may be applied to other imaging modes of the ultrasound machine 5 for moving structure, for any estimated parameter (e.g. velocity, strain rate, power, amplitude, etc.).

In summary, certain embodiments of the present invention afford an approach to more easily visualize tissue motion parameter information, such as tissue velocity and strain rate, in a two-dimensional ultrasound image such that more of the tissue motion parameter information is broken out and observed. Adaptive mapping of movement parameter data to a color characteristic legend based on the distribution of the movement parameter data accomplishes the desired result.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. In an ultrasound machine for generating an image responsive to moving structure within a region of interest of a subject by displaying at least one color characteristic corresponding to a movement parameter of said structure, apparatus for mapping said color characteristic comprising:
a front-end arranged to transmit ultrasound waves into said structure and to generate received signals in response to ultrasound waves backscattered from said structure in said region of interest over a time period;
a processor responsive to: (i) said received signals to generate a set of parameter signals representing values of said movement parameter within said structure during said time period, (ii) a distribution of said set of parameter signals, and (iii) a mapping algorithm to generate a set of color characteristic signals representative of said values of said movement parameter, wherein said mapping algorithm comprises a mapping function formed by generating a cumulative total of a frequency of occurrence of said values of said movement parameter, and normalizing said cumulative total to a domain of a color characteristic legend resulting in a uniform distribution of said values of said movement parameter across said domain of said color characteristic legend; and
a display arranged to display a color representation of said moving structure in response to said set of color characteristic signals.

2. The apparatus of claim 1 wherein said moving structure comprises cardiac tissue.

3. The apparatus of claim 1 further comprising a user interface arranged to enable an operator to select said region of interest from said image on a monitor.

4. The apparatus of claim 1, wherein said movement parameter comprises one of velocity and strain rate.

5. The apparatus of claim 1, wherein said color characteristic comprises hue.

6. The apparatus of claim 1, wherein said time period comprises at least a portion of a cardiac cycle.

7. The apparatus of claim 1 wherein said distribution of said set of parameter signals comprises a histogram representing said frequency of occurrence of said values of said movement parameter.

8. The apparatus of claim 7 wherein said mapping algorithm generates a mapping function comprising a cumulative total of the occurrence of said values of said histogram.

9. The apparatus of claim 8 wherein at least one of said histogram and said mapping function is weighted.

10. The apparatus of claim 1, wherein said color representation of said moving structure in response to said set of color characteristic signals uses a full dynamic range of the color map, wherein said full dynamic range of the color map includes a continuous range of color hues from red to violet.

11. The apparatus of claim 1, wherein said mapping function is used by said processor as a non-linear transfer function between said values of said movement parameter and said set of color characteristic signals.

12. In an ultrasound machine for generating an image responsive to moving structure within a region of interest of a subject by displaying at least one color characteristic corresponding to a movement parameter of said structure, a method of mapping said color characteristic comprising:
transmitting ultrasound waves into said structure and generating received signals in response to ultrasound waves backscattered from said structure in said region of interest over a time period;
generating a set of parameter signals representing values of said movement parameter within said structure during said time period in response to said received signals;
generating a set of color characteristic signals representative of said values of said movement parameter in response to: (i) a distribution of said set of parameter signals and (ii) a mapping algorithm that generates a cumulative total of a frequency of occurrence of said values of said movement parameter, and normalizing said cumulative total to a domain of a color characteristic legend resulting in a uniform distribution of said values of said movement parameter across said domain of said color characteristic legend; and
displaying a color representation of said moving structure in response to said set of color characteristic signals.

13. The method of claim 12 wherein said moving structure comprises cardiac tissue.

14. The method of claim 12 and further comprising enabling an operator to select said region of interest from said image.

15. The method of claim 12 wherein said movement parameter comprises one of velocity and strain rate.

16. The method of claim 12 wherein said color characteristic comprises hue.

17. The method of claim 12 wherein said time period comprises at least a portion of a cardiac cycle.

18. The method of claim 12 wherein said distribution of said set of parameter signals comprises a histogram representing said frequency of occurrence of said values of said movement parameter.

19. The method of claim 18 wherein said mapping algorithm generates a mapping function comprising a cumulative total of the occurrence of values of said histogram.

20. The method of claim 19 wherein at least one of said histogram and said mapping function is weighted.

21. The method of claim 12, wherein said color representation of said moving structure in response to said set of color characteristic signals uses a full dynamic range of the color map, wherein said full dynamic range of the color map includes a continuous range of color hues including red, orange, yellow, green, blue, and violet.

22. The method of claim 12, further comprising using a mapping function of the mapping algorithm as a non-linear transfer function between said values of said movement parameter and said set of color characteristic signals.

* * * * *